United States Patent
Saulnier et al.

(10) Patent No.: US 7,701,227 B2
(45) Date of Patent: Apr. 20, 2010

(54) HIGH PRECISION VOLTAGE SOURCE FOR ELECTRICAL IMPEDANCE TOMOGRAPHY

(75) Inventors: Gary J. Saulnier, East Greenbush, NY (US); Ning Liu, Troy, NY (US); Alexander S. Ross, Albany, NY (US)

(73) Assignee: Rensselaer Polytechnic Institute, Troy, NY (US)

(*) Notice: Subject to any disclaimer, the term of this patent is extended or adjusted under 35 U.S.C. 154(b) by 0 days.

(21) Appl. No.: 11/722,159

(22) PCT Filed: Dec. 30, 2005

(86) PCT No.: PCT/US2005/047477
§ 371 (c)(1),
(2), (4) Date: Jun. 19, 2007

(87) PCT Pub. No.: WO2006/074092
PCT Pub. Date: Jul. 13, 2006

(65) Prior Publication Data
US 2008/0001608 A1    Jan. 3, 2008

Related U.S. Application Data

(60) Provisional application No. 60/641,508, filed on Jan. 5, 2005.

(51) Int. Cl.
*G01R 35/00* (2006.01)
*G01R 27/02* (2006.01)
*A61B 5/05* (2006.01)

(52) U.S. Cl. .................. 324/601; 324/605; 600/547

(58) Field of Classification Search ............... 324/601, 324/202, 130, 74, 713, 691, 522, 426, 439, 324/444, 603, 605; 600/547
See application file for complete search history.

(56) References Cited

U.S. PATENT DOCUMENTS

| | | | | |
|---|---|---|---|---|
| 5,012,181 A * | 4/1991 | Eccleston | .................... | 324/74 |
| 5,544,662 A * | 8/1996 | Saulnier et al. | .............. | 600/547 |
| 6,281,687 B1 * | 8/2001 | Shepston | .................... | 324/601 |
| 6,940,286 B2 * | 9/2005 | Wang et al. | .................. | 324/450 |
| 2003/0184459 A1 * | 10/2003 | Engl | .......................... | 341/120 |
| 2005/0251062 A1 * | 11/2005 | Choi et al. | .................. | 600/547 |
| 2007/0132617 A1 * | 6/2007 | Le | .............................. | 341/120 |
| 2007/0152863 A1 * | 7/2007 | Le et al. | ..................... | 341/155 |

* cited by examiner

*Primary Examiner*—Hoai-An D Nguyen
(74) *Attorney, Agent, or Firm*—Notaro & Michalos P.C.

(57) ABSTRACT

An EIT system includes a plurality of voltage sources for supplying a corresponding plurality of voltages to a corresponding number of other structures, voltage source calibration means for calibrating each voltage source, and switching means for individually connecting the calibration means to each voltage source in succession during a period when each other structure is in an inactive condition. Calibrating respective voltages and currents for each voltage source compensates for shunt impedance of each voltage source. A method for calibrating the system includes individually connecting the calibration means to each voltage source in succession during a period when each other structure is in an inactive condition for calibrating all of said voltage sources in the same way.

20 Claims, 12 Drawing Sheets

HIGH PRECISION VOLTAGE SOURCE FOR ELECTRICAL IMPEDANCE TOMOGRAPHY

CROSS-REFERENCE TO RELATED APPLICATION

This U.S. patent application claims priority on, and all benefits available from U.S. provisional patent application 60/641,508 filed Jan. 5, 2005, all of which is incorporated here by reference.

STATEMENT OF GOVERNMENT INTEREST

Development of the present invention was supported, in part, by CenSSIS, the Center for Subsurface Sensing and Imaging Systems, under the Engineering Research Center Program of the National Science Foundation (Award number EEC-9986821).

FIELD AND BACKGROUND OF THE INVENTION

The present invention relates generally to the field of EIT, and in particular to a new and useful electrical impedance imaging apparatus and a method for calibrating the electrical impedance imaging apparatus.

Electrical impedance tomography is an imaging modality which displays the spatial distribution of the complex conductivity distribution inside a body. An excitation is applied to electrodes on the body surface, resulting in an electromagnetic (EM) field appearing within the volume. If the excitation consists of one or more currents, the voltages that appear at some or all of the electrodes are measured. If the excitation consists of voltages, then the currents at the electrodes are measured. The inverse problem describing the current to voltage relationship is then solved to determine the complex conductivity distribution that must have been present to produce the measured data set. The ill-posedness of this inverse problem manifests itself through the small changes in surface current or voltage that sometimes result from large changes in the interior impedance distribution. High precision electronics are needed to apply the excitations and measure the data that correspond to these changes.

For an electrical impedance tomograph with finite measurement precision, distinguishability is defined as the ability to detect an inhomogeneity in a homogeneous background, and is maximized for all conductivities and geometries when currents are applied to the surface electrodes and the resulting voltages are measured. Furthermore, distinguishability is maximized when multiple, independent current sources are used to apply spatial patterns of currents to the electrodes. Applying current patterns whose eigenvalues match the natural response (modes) of the body being interrogated maximizes the signal to noise ratio (SNR) of the resulting data set and therefore minimizes the amount of regularization necessary for the subsequent reconstruction.

Taken together, these two observations suggest that multiple, high-precision current sources are required to maximize the distinguishability and SNR of an impedance tomography data set. While such current sources have been developed for this application, they tend to have limited bandwidth, apply only sinusoidal excitations, and require a large number of high precision components. (See [1] R. D. Cook, G. J. Saulnier, D. G. Gisser, J. C. Goble, J. C. Newell, and D. Isaacson. ACT3: A high-speed, high-precision electrical impedance tomograph. *IEEE Transactions on Biomedical Engineering*, vol. 41 (8): 713-722, August 1994; Also see [2] A. S. Ross, G. J. Saulnier, J. C. Newell, and D. Isaacson. Current source design for electrical impedance tomography. *Physiological Measurement*, vol. 24(2):509-516, May 2003.) The result is an electronics package with a large system footprint, and high component, power, and cooling costs.

In contrast, precision voltage sources are generally easier and less costly to implement. However, as mentioned above, applying voltages and measuring currents produces a less optimal EIT system. In an attempt to gain the hardware simplicity of a voltage source along with the optimality of applied currents, algorithms have been developed for utilizing multiple voltage sources to apply a desired current pattern (See [3] M. H. Choi, D. Isaacson, G. J. Saulnier, and J. C. Newell. An iterative approach for applying multiple currents to a body using voltage sources in electrical impedance tomography. In *Proceedings of the 25th Annual International Conference of the IEEE Engineering in Medicine and Biology Society*, volume 4, pages 3114-3117, September 2003.) This algorithm takes into account the interaction between the sources which results in the current at any given electrode being a function of the voltages on all the electrodes.

When using a voltage source in EIT, it is necessary to know both the applied voltage and the resulting current with high precision. If it is desired to have the applied voltage remain unchanged for a wide range of load impedances, then it is necessary to have a voltage source with low output impedance. In the case where voltages are being applied to produce specific currents, the applied voltage will be adjusted, generally in an iterative way, to compensate for changes in the load impedance. Consequently, low output impedance less important than having the ability to precisely measure the actual applied voltage and current.

SUMMARY OF THE INVENTION

It is an object of the present invention to provide a system and method for using voltage sources to produce a desired current pattern in an EIT system.

It is a further object of the present invention to directly measure the actual applied voltage and resulting current in an EIT system with high precision.

It is yet another object of the present invention to measure the actual applied voltage and resulting current in an EIT system with high accuracy.

Accordingly, a voltage source circuit, calibration circuit and calibration procedure are provided for use in EIT. The source incorporates direct measurement of the applied voltage and measurement of the applied current. The calibration procedure results in a set of calibration factors and parameters that allow the suppression of errors due to stray shunt impedance, passive element values and non-ideal properties of active devices. Since all voltage sources in an EIT system will be calibrated using a single calibration circuit, the approach results in nearly identical performance of all voltage sources.

The EIT system of the present invention includes a plurality of voltage sources for supplying a corresponding plurality of voltages to a corresponding number of other structures, voltage source calibration means for calibrating each voltage source, and switching means for individually connecting the calibration means to each voltage source in succession during a period when each other structure is in an inactive condition. Each voltage source includes an operational amplifier having an output and a sense resistor connected to the output of the operational amplifier. Each voltage source also includes a buffer amplifier having an input connected to the sense resistor for outputting a measured voltage, and an instrumentation amplifier having one input connected to the operational amplifier output and another input connected to the sense resistor for outputting a measured current. The calibration circuit includes an operational amplifier, a buffer amplifier, and switching means for selectively connecting an output of each voltage source to only one of the operational and buffer amplifiers to compensate for shunt impedance of each voltage source.

The method for calibrating the system includes individually connecting the calibration means to each voltage source in succession during a period when each other structure is in an inactive condition for calibrating all of said voltage sources in the same way. The method includes the steps of determining a gain for the buffer amplifier, determining a gain for the instrumentation amplifier, determining a value for the sense resistor, determining an output shunt impedance for each voltage source, and determining an actual current delivered to the body by the voltage source.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
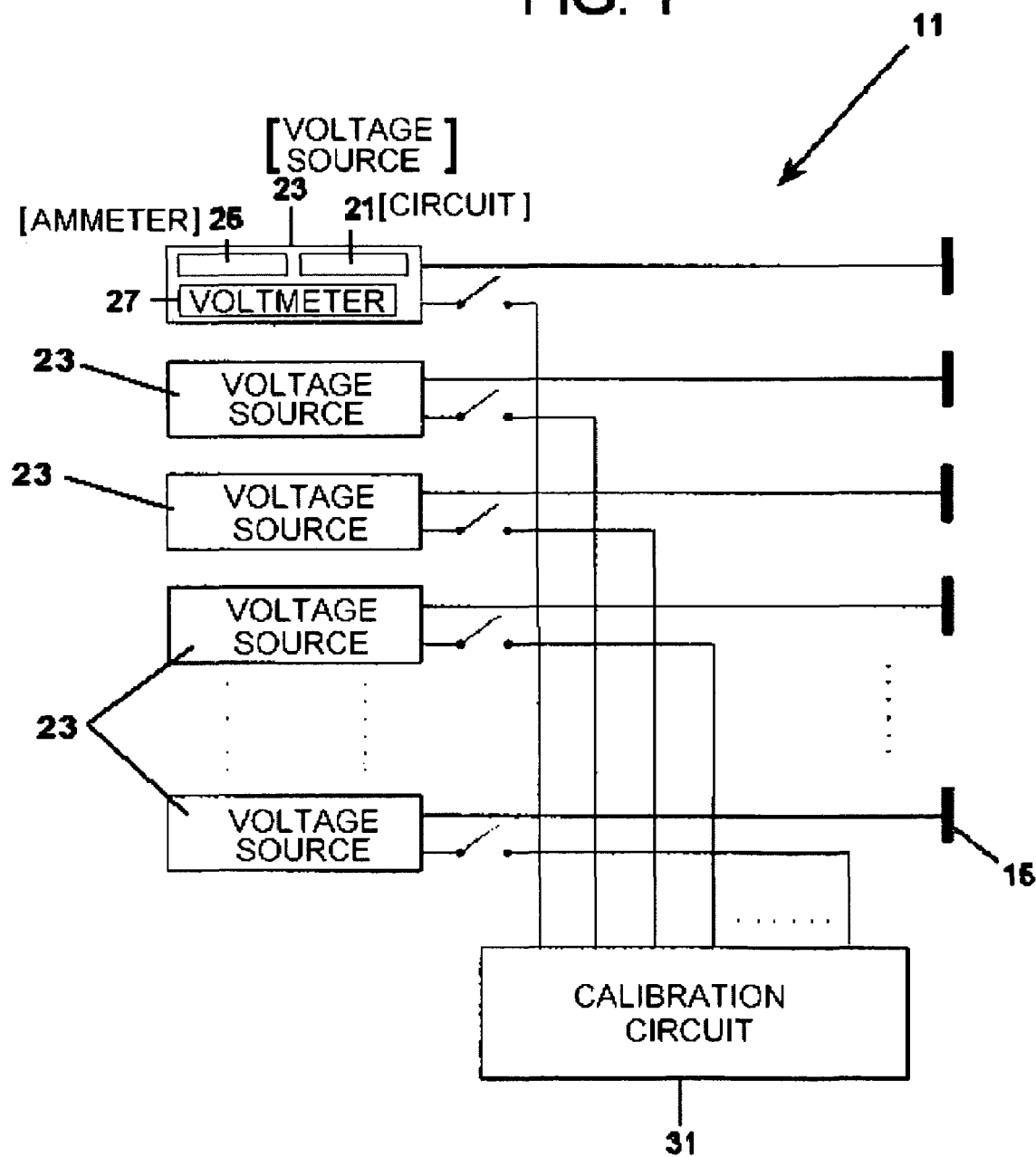
FIG. 1 is a block diagram of an applied-voltage EIT system with L number of electrodes.

Referring now to the drawings, in which like reference numerals are used to refer to the same or similar elements, FIG. 1 is a block diagram of an applied-voltage EIT system 11 with L number of electrodes 15. Each electrode 15 is connected to a circuit 21 that includes a voltage source 23 for generating the applied voltage as well as an ammeter 25 to measure the applied current and a voltmeter 27 to directly measure the applied voltage. A switching network enables a single calibration circuit to be connected to any of the voltage source/ammeter/voltmeter circuits 21 to allow the whole system 11 to be calibrated to a single reference.

Though not shown in FIG. 1, the voltage sources 23 (with ammeters 25 and voltmeters 27), switches, and calibration circuit 31 each interface to a digital controller which sets the system configuration and collects digital measurements of voltage and current. A series of calibration steps, to be described below, are performed to collect calibration data for each source 23. Typically, the electrodes 15 are not in contact with a body to be imaged during these calibration steps. The digital controller utilizes the calibration data to determine actual applied currents and voltages from measurements that are made when collecting data for an EIT image.

Figure 2:
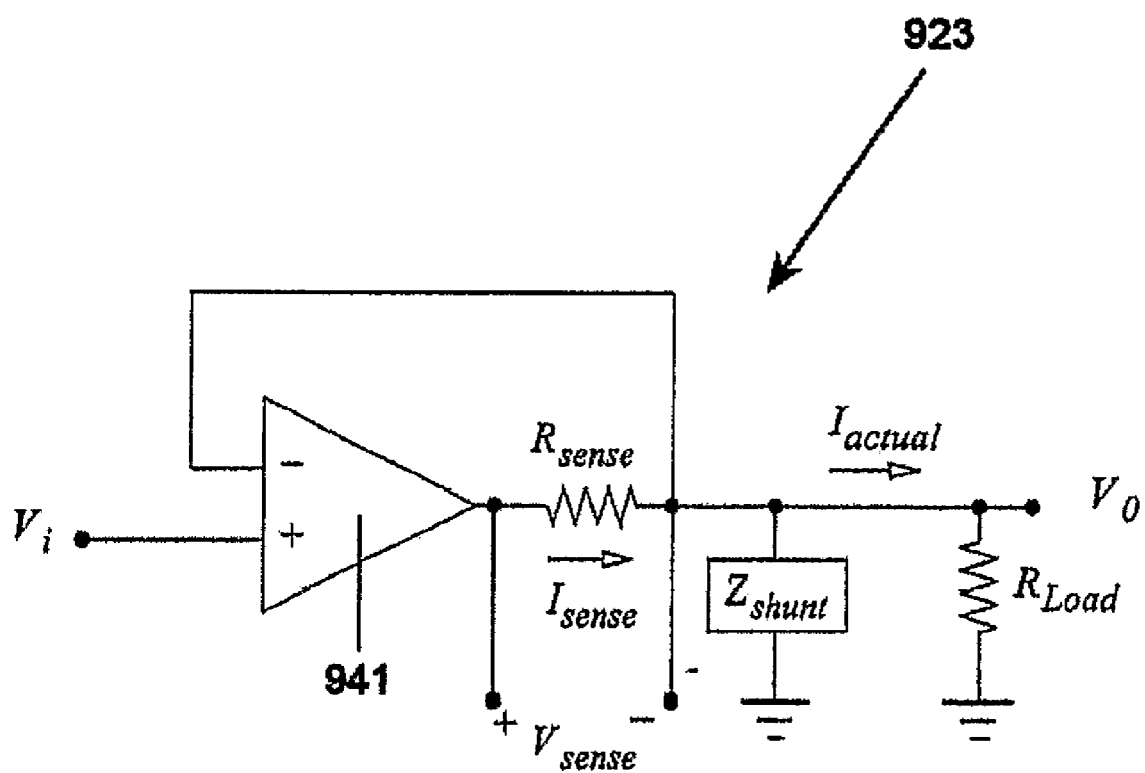
FIG. 2 is a schematic circuit diagram of a voltage source with a current measuring capability.

FIG. 2 shows one embodiment for implementing a voltage source 923 with an integrated current measurement capability. The voltage source 923 provides a voltage $V_i$ at an operational amplifier 941, which is part of a measuring circuit that also includes a current-sensing resistor, $R_{sense}$, included in the feedback loop. The operation amplifier 941 is a buffer amplifier, and specifically a unity gain buffer because the voltage that is transferred is unchanged. The measuring circuit also includes a shunt impedance, $Z_{shunt}$, and a load resistance, $R_{load}$. The signal, $I_{actual}$, is the measure of the actual current that is going to the load while the output voltage, $V_o$, is produced.

In one exemplary case, the shunt impedance, $Z_{shunt}$, is infinite and the operational amplifier 941 is ideal, having infinite gain, infinite input resistance and zero input capacitance. Under these conditions, the voltage, $V_a$, that is applied to the load resistance, $R_{Load}$, equals the input voltage, $V_i$. Also, the current delivered to the load, $I_{actual}$, equals the current through $R_{sense}$, denoted as $I_{sense}$. This load current can be determined by measuring $V_{sense}$ and evaluating $I_{sense} = V_{sense}/R_{sense}$.

If the operational amplifier has finite gain, $V_o \neq V_i$ and it is necessary to directly measure $V_o$ in a high-precision application. The introduction of $Z_{shunt}$ creates a larger problem because it causes $I_{sense}$ to be different from $I_{actual}$. $Z_{shunt}$ can include the capacitance introduced by wiring, printed-circuit board traces, and the input capacitance and resistance at the operational amplifier's non-inverting terminal. Also, the addition of other circuits, such as a voltmeter, connected to the output will insert additional capacitance and finite shunt resistance which can be grouped in $Z_{shunt}$. In all cases, the presence of finite impedance to ground will result in some of $I_{sense}$ flowing to ground through $Z_{shunt}$ rather than into $R_{Load}$. The error current is denoted by $$I_{error} = I_{sense} - I_{actual} = \frac{V_0}{Z_{shunt}}. \qquad (1)$$

Rearranging, equation 2 is derived:

$$I_{actual} = I_{sense} - \frac{V_0}{Z_{shunt}} \qquad (2)$$

meaning that knowledge of $Z_{shunt}$, $V_o$ and $I_{sense}$ enables the computation of the actual load current value.

Figure 3:
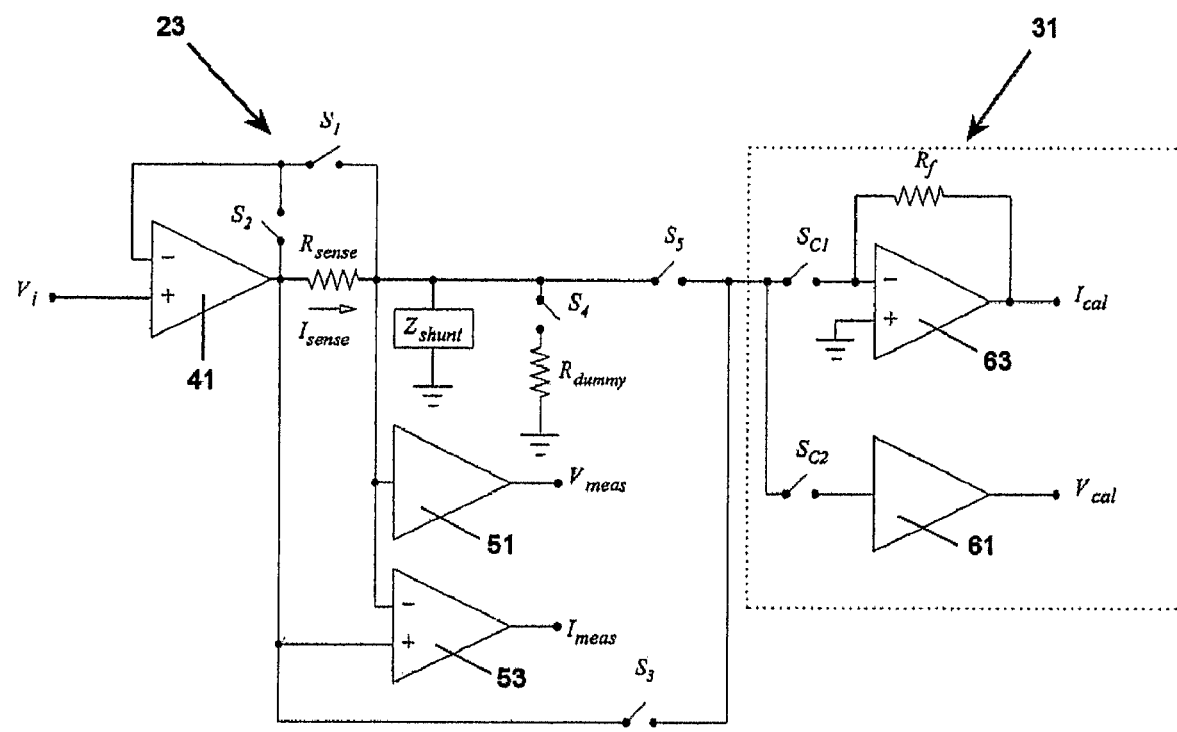
FIG. 3 is a schematic circuit diagram of a voltage source with a current measuring capability and a calibration circuit for allowing precision voltage and current measurements.

The voltage source and calibration circuit described below in conjunction with FIG. 3 will be able to directly measure $Z_{shunt}$ in order to enable $I_{actual}$ to be determined with high precision. FIG. 3 shows an improvement to the voltage source to enable calibration. In addition to a number of switches, a buffer amplifier (Buffer) 51 has been added to allow measurement of the output voltage and an instrumentation amplifier (IA) 53 has been added for determining the current flowing in $R_{sense}$. A calibration circuit 31 has also been added that can measure either current or voltage. The calibration circuit 31 includes an operational amplifier 63 and a buffer amplifier 61. The operational amplifier 63 is assumed to have a frequency independent transresistance of $R_f$ and the voltage buffer is assumed to have a gain of unity.

In a complete system, there is only one calibration circuit 31 and individual voltage sources 23 can be connected to this calibration circuit 31, one at a time. It is assumed that the calibration circuit 31 is itself calibrated to a standard, i.e. the current or voltage values that it reports are the true values. However, since all voltage sources are calibrated using a single calibration circuit, errors in the calibration circuit will only impact the overall accuracy of the system and not its precision.

The shunt impedance, $Z_{shunt}$ includes any stray capacitance along with input capacitance and resistance for the instrumentation amplifier 53, buffer amplifier 51 and the voltage source 23 itself. Also included is the switch capacitance to ground. The capacitance of solid-state switches tends to be large and vary significantly with switch position and applied voltage. Since switch positions will change between calibration settings and operation setting, low-capacitance reed relays are used in place of solid-state switches. Reed relays present capacitance that varies little with switch position. Additionally, it is assumed that the "on" resistance of the switches is negligible.

There are several steps for calibrating the voltage source 23. During the calibration process, the gains of the buffer amplifier 51 and the instrumentation amplifier 53 are measured along with the precise values of $R_{sense}$ and $Z_{shunt}$. It is assumed that phase-sensitive voltmeters are able to measure the voltages $V_{meas}$, $I_{meas}$, $V_{cal}$ and $I_{cal}$. Consequently, all gains, voltages, currents and impedance values can be complex. The 4 steps in the calibration algorithm are explained below.

Figure 4:
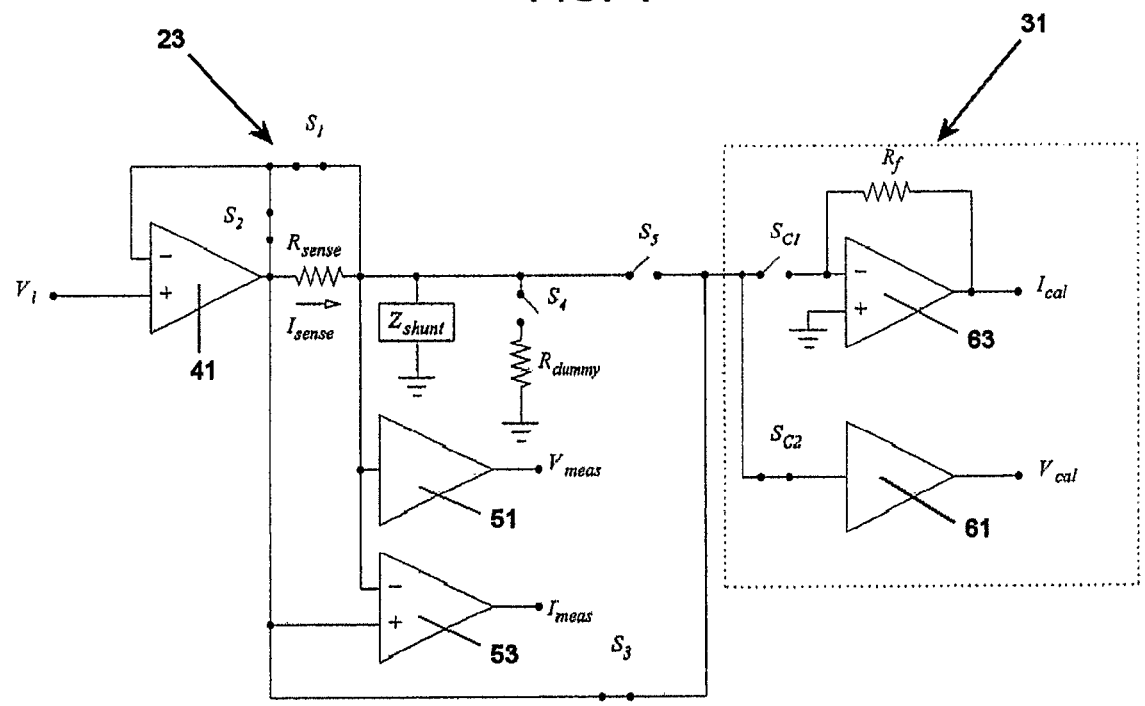
FIG. 4 is a schematic circuit diagram according to FIG. 3 and further showing the switch setting for the first step in the calibration method.

FIG. 4 shows the switch settings for step one of the calibration process. In this configuration, switches $S_1$, $S_2$, $S_3$ and $S_{C2}$ are closed and all other switches are open. With $S_1$ closed, $R_{sense}$ is shorted; with $S_2$ closed, the voltage source operating amplifier 41 is configured as a unity gain buffer. $S_3$ and $S_{C2}$ connect the voltage source operating amplifier 41 output, which is also the input to the buffer amplifier 51 and both inputs to the instrumentation amplifier 53, to the calibration circuit voltmeter.

An input voltage, $V_i$, is applied and the voltages $V_{cal}$, $V_{meas}$, and $I_{meas}$ are measured. From these measurements, the following gains can be determined:

$$G_{Buffer} = \frac{V_{meas}}{V_{cal}} \qquad (3)$$

$$G_{IA-CM} = \frac{I_{meas}}{V_{cal}}.$$

where $G_{Buffer}$ is the gain of the Buffer amplifier 51 and $G_{IA-CM}$ is the common-mode gain of the instrumentation amplifier 53. In general, the output of an instrumentation amplifier 53 is determined by $$I_{meas} = G_{IA-DM}(V_+ - V_-) + G_{IA-CM}\left(\frac{V_+ + V_-}{2}\right) \qquad (4)$$

where $G_{IA-OM}$ is the differential gain, $V_+ - V_-$ is the differential input voltage and $$\frac{V_+ + V_-}{2}$$

is the common-mode input voltage. Common-mode gain can be determined because the two inputs to the instrumentation amplifier 53 are at the same voltage (connected by $S_1$), meaning that the differential input voltage is zero.

Figure 5:
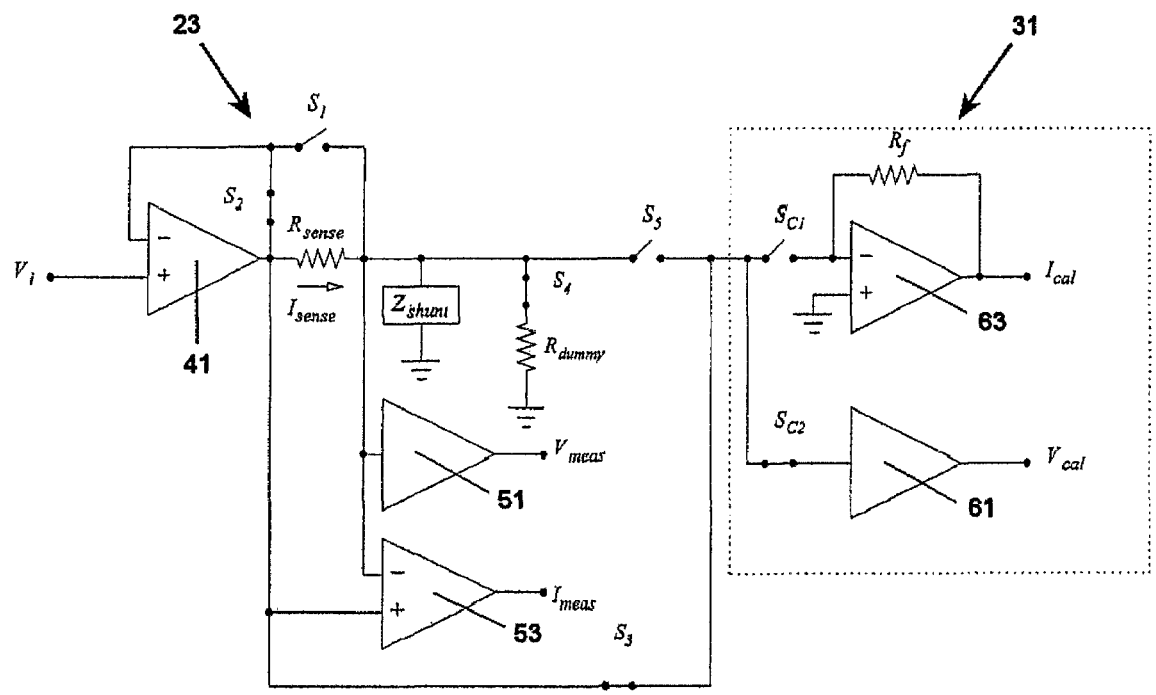
FIG. 5 is a schematic circuit diagram according to FIG. 3 and further showing the switch setting for the second step in the calibration method.

In the second calibration step, the differential gain of the instrumentation amplifier 53, $G_{IA-OM}$ is determined. FIG. 5 shows the switch arrangement for this step. As can be observed, switches $S_2$, $S_3$, $S_4$ and $S_{C1}$ are closed and all other switches are open. Opening $S_1$ and closing $S_4$ produces a voltage drop across $R_{sense}$ when an input voltage, $V_i$, is applied which appears as a differential input voltage to the instrumentation amplifier 53. The input voltage at the non-inverting input is measured by the calibration circuit and equals $$V_+ = V_{cal} \qquad (5)$$

while the voltage at the non-inverting input is $$V_- = \frac{V_{meas}}{G_{Buffer}}. \qquad (6)$$

The differential input voltage, then, is $$V_{DM} = V_+ - V_- = V_{cal} - \frac{V_{meas}}{G_{Buffer}} \qquad (7)$$

and the common mode input voltage is $$V_{CM} = \frac{V_+ + V_-}{2} = \frac{1}{2}\left(V_{cal} + \frac{V_{meas}}{G_{Buffer}}\right) \qquad (8)$$

Using equation 4, equation 9 can be solved for:

$$G_{IA-DM} = \frac{I_{meas} - G_{IA-CM} V_{CM}}{V_{DM}} \quad (9)$$

and, using this result in combination with equations 7 and 8, $G_{IA-DM}$ can be computed.

Figure 6:
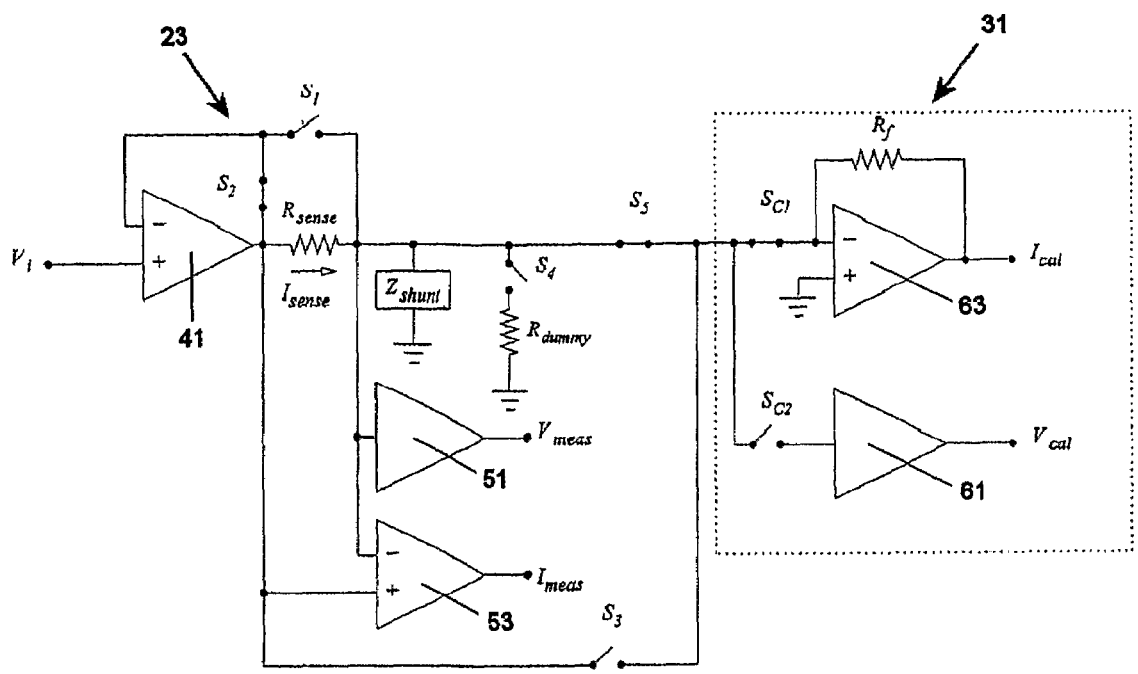
FIG. 6 is a schematic circuit diagram according to FIG. 3 and further showing the switch setting for the third step in the calibration method.

FIG. 6 shows the configuration for the third step in the calibration process. Here, switches $S_2$, $S_5$ and $S_{C1}$ are closed and all other switches are open. Operational amplifier 63 in the calibration circuit is configured as a current-to-voltage converter (I-V converter) which, for an ideal operational amplifier, produces an output voltage that equals $-Rf$ times the input current (current in $S_{C1}$). Additionally, with an ideal operational amplifier and negative feedback the voltage at the inverting operational amplifier input terminal is forced to equal the voltage at the non-inverting input terminal which is at ground potential. This "virtual ground" in the arrangement of FIG. 6 results in both ends of $Z_{shunt}$ ideally being at ground potential. When implemented with a real operational amplifier, the circuit will result in a small voltage appearing across $Z_{shunt}$. A calibration algorithm will account for this voltage in determining values for $R_{sense}$ and $Z_{shunt}$.

In this step, the voltages $I_{cal}$, $V_{meas}$ and $I_{meas}$ are recorded. For clarity, these quantities will be denoted as $I_{cal\_3}$, $V_{meas\_3}$ and $I_{meas\_3}$. In addition, the differential voltage across $R_{sense}$ is computed using $$V_{DM\_3} = \frac{I_{meas\_3} - G_{IA-CM}\left(\frac{V_{meas\_3}}{G_{Buffer}}\right)}{\left(G_{IA-DM} + \frac{G_{IA-CM}}{2}\right)}. \quad (10)$$

Since the current through $R_{sense}$ equals the current in $Z_{shunt}$ plus the current in the I-V converter, equation 11 can be derived.

$$\frac{V_{DM\_3}}{R_{sense}} = -\frac{I_{cal\_3}}{R_f} + \frac{V_{meas\_3}}{G_{Buffer} Z_{shunt}}. \quad (11)$$

Figure 7:
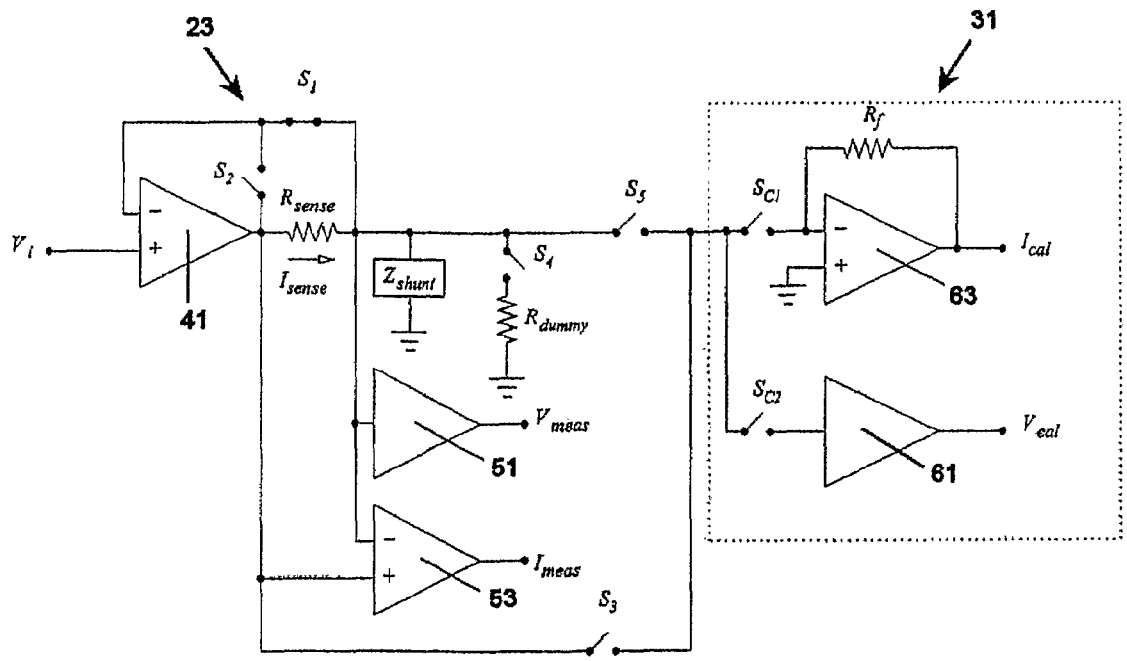
FIG. 7 is a schematic circuit diagram according to FIG. 3 and further showing the switch setting for the fourth step in the calibration method.

FIG. 7 shows the switch configuration for the last step in the calibration. This configuration is also employed when using the voltage source after calibration. Here, only $S_1$ is closed; all other switches are open. A voltage $V_i$ is applied and both $I_{meas}$ and $V_{meas}$ are measured and denoted as $I_{meas\_4}$ and $V_{meas\_4}$. Likewise, the differential voltage across $R_{sense}$ is computed using equation 12:

$$V_{DM\_4} = \frac{I_{meas\_4} - G_{IA-CM}\left(\frac{V_{meas\_4}}{G_{Buffer}}\right)}{\left(G_{IA-DM} + \frac{G_{IA-CM}}{2}\right)}. \quad (12)$$

The current through $R_{sense}$ flows in $Z_{shunt}$, resulting in equation 13:

$$\frac{V_{DM\_4}}{R_{sense}} = \frac{V_{meas\_4}}{G_{Buffer} Z_{shunt}}. \quad (13)$$

In a high precision application, the deviation of the value of $R_{sense}$ from its nominal value and its variation with aging and temperature will significantly degrade performance. Using the results from steps 3 and 4, along with the calibration constants from steps 1 and 2, the values of both $R_{sense}$ and $Z_{shunt}$ can be estimated.

Substituting (13) into (11) gives equation 14:

$$\frac{V_{DM\_3}}{R_{sense}} = -\frac{I_{cal\_3}}{R_f} + \frac{V_{meas\_3}}{V_{meas\_4}} \frac{V_{DM\_4}}{R_{sense}} \quad (14)$$

which can be solved for $R_{sense}$ producing equation 15:

$$R_{sense} = \left(\frac{R_f}{I_{cal\_3}}\right)\left(\frac{V_{meas\_3}}{V_{meas\_4}} V_{DM\_4} - V_{DM\_3}\right). \quad (15)$$

Finally, $Z_{shunt}$ can be computed using equation 13 rearranged as equation 16:

$$Z_{shunt} = \frac{V_{meas\_4} R_{sense}}{G_{Buffer} V_{DM\_4}}. \quad (16)$$

These values of $R_{sense}$ and $Z_{shunt}$ can be stored and used to determine the current being delivered the load in an actual voltage source application.

Figure 8:
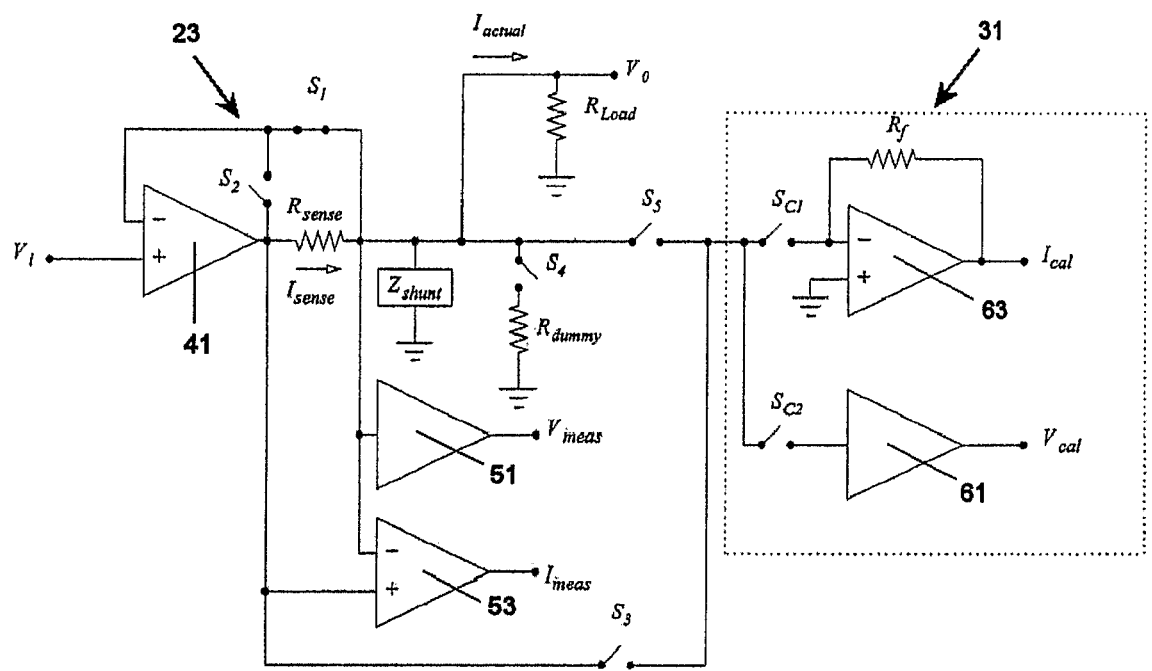
FIG. 8 is a schematic circuit diagram according to FIG. 3 and further showing the configuration for applying the voltage source.

In operation, the goal is have precise measurements of the voltage applied to a load and the current delivered to this load. FIG. 8 shows the configuration, with the delivered current denoted as $I_{actual}$ and the applied voltage denoted as $V_o$. The voltage at the load, $V_o$, is determined by $$V_o = V_{meas}/G_{Buffer} \quad (17)$$

The current being delivered to the load, factual is found using equation 2 with $V_o$, given by equation 17, $$I_{actual} = I_{sense} - \frac{V_0}{Z_{shunt}} \quad (18)$$

$$= \frac{I_{meas} - G_{IA-CM}\left(\frac{V_{meas}}{G_{Buffer}}\right)}{\left(G_{IA-DM} + \frac{G_{IA-CM}}{2}\right) R_{sense}} - \frac{V_{meas}}{G_{Buffer} Z_{shunt}}. \quad (19)$$

Circuit Simulation

The circuit topology shown in FIG. 8 was implemented in PSpice to provide data to demonstrate the behavior of the calibration algorithm. A model for an Analog Devices AD8610 operational amplifier was used to implement the voltage source, the I-V converter, and the voltage buffers. The AD8610 was configured as a voltage follower to implement the voltage buffers. A model for a Burr-Brown (Texas Instruments) PGA207 high-speed programmable gain instrumentation amplifier was used for the instrumentation amplifier. This instrumentation amplifier was configured for unity differential gain and the model provides a common-mode rejection ratio (CMRR) of approximately 100 dB at DC with a single pole roll-off with a pole at approximately 4 kHz. The I-V converter used a feedback resistance of 1 kΩ. A 50 pF capacitor was added in parallel with $R_f$ to improve stability.

Figure 9:
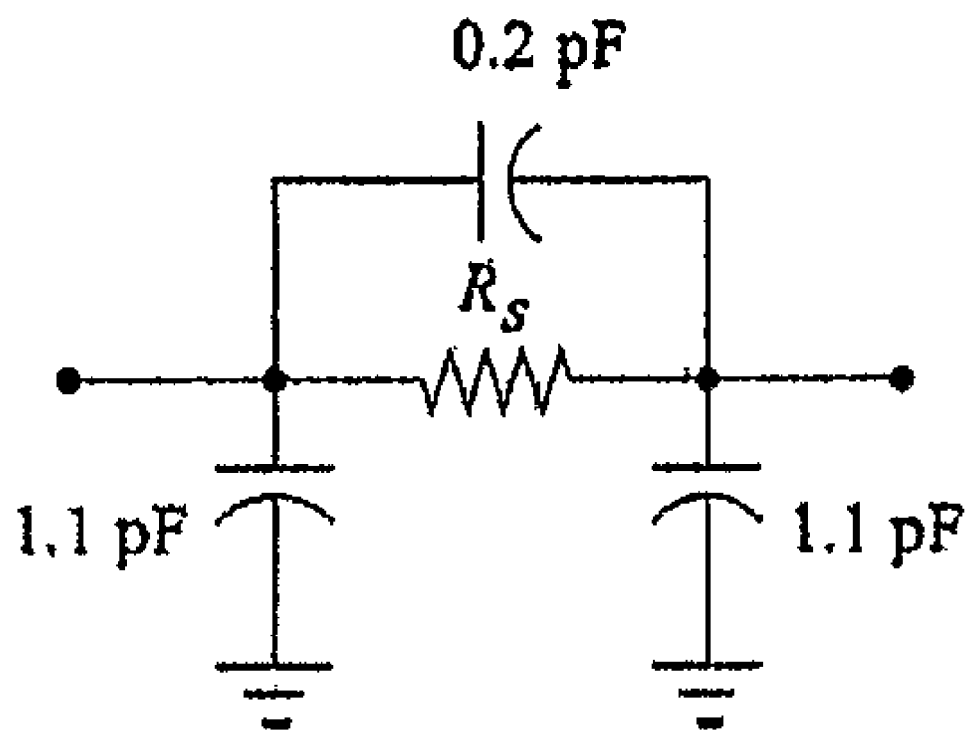
FIG. 9 is a schematic reed relay model where the contact resistance, $R_s$, is $0.150\Omega$ when the switch is "on" and $1G\Omega$ when the switch is "off"

The switches, assumed to be reed relays, were modeled as shown in FIG. 9. The model is based on the specifications for the Coto Technology 9401 surface mount relay. These relays present 1.1 pF of capacitance between each open contact to the coil and 0.2 pF across open contacts. Contact resistance has a maximum value of 0.15Ω.

The performance of the calibration algorithm was evaluated by collecting values for $V_{meas}$, $I_{meas}$, $I_{cal}$, and $V_{cal}$ as needed for each of the 4 calibration steps defined above (with $R_{Load}=\infty$). Additionally, values for $V_{meas}$ and $I_{meas}$ were collected with $R_{Load}$ present. From this data, an estimate of $R_{Load}$ was produced and compared to the actual $R_{Load}$. All measured voltages are complex and the estimate of $R_{Load}$ is a complex impedance which can be viewed as the parallel combination of a resistance and capacitance, where the capacitance can be positive or negative and ideally equals zero. Separate estimates for $R_{Load}$ were generated for various instances of the voltage source having different values of $Z_{shunt}$ and/or $R_{sense}$. The calibration circuit was not changed at any time in order to accurately model the case where multiple voltage sources, each having somewhat different properties due to component variation and differences in physical layout, are calibrated using a single calibration circuit.

The parameters for the 3 test cases are shown in Table 1. The shunt impedance, $Z_{shunt}$ is modeled as the parallel combination of $R_{shunt}$ and $C_{shunt}$. Case 1 is a reference case, having a $R_{sense}$ with the nominal value of 1 kΩ and a significant capacitive component to $Z_{shunt}$. Case 2 is used to illustrate the ability of the calibration algorithm to compensate for the variation in the true value of $R_{sense}$ from the nominal value. Case 3 has a substantially different value for $Z_{shunt}$ and is used to illustrate the ability to compensate for differences in shunt impedance.

TABLE 1

Parameters for the 3 test cases

|  | $R_{sense}$ | $R_{shunt}$ | $C_{shunt}$ |
|---|---|---|---|
| Case 1 | 1 kΩ | 10 MΩ | 150 pF |
| Case 2 | 1.1 kΩ | 10 MΩ | 150 pF |
| Case 3 | 1 kΩ | 1 MΩ | 300 pF |

No Calibration: FIG. 10 shows the error in the estimated load impedance when the three voltage sources, i.e. the three cases in Table 1, are operated without calibration. $R_{sense}$ is assumed to be equal to its nominal value of 1 kΩ, the instrumentation amplifier is assumed to have unity differential gain and zero common-mode gain, the voltage buffer is assumed to have unity gain, and $Z_{shunt}$ is assumed to be infinite. The load impedance is a pure resistance of value 1 kΩ.

Figure 10A:
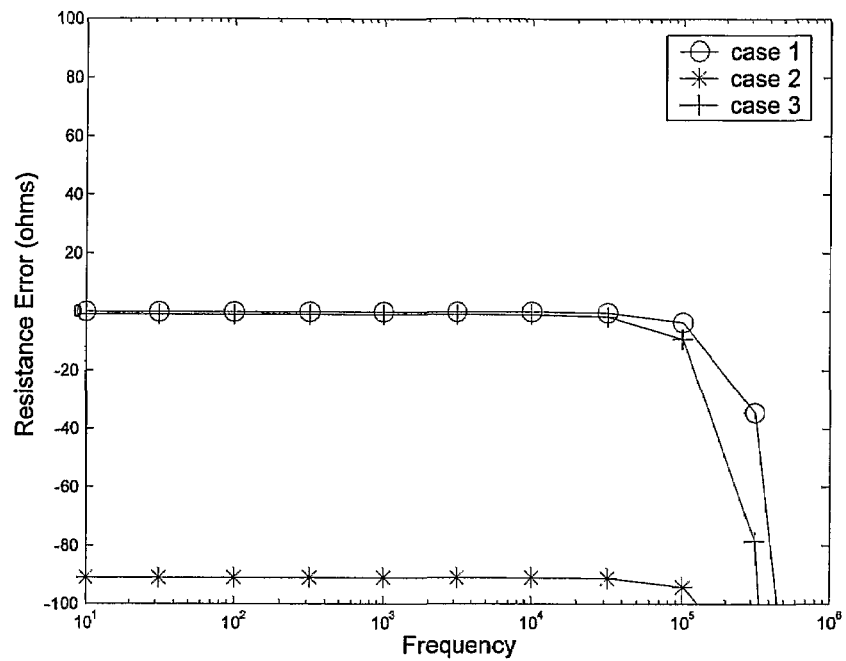
FIG. 10a is a graph showing the error in the estimated load resistance when three sample voltage sources are operated without calibration according to a simulation.

FIG. 10(a) shows error in the estimated load resistance. At low frequencies, the errors for Cases 1 and 3 are small (approximately −0.08Ω and −1Ω, respectively) due to the fact that $R_{sense}$ is equal to the assumed value of 1 kΩ and the primary source of error is Rshunt (10 MΩ and 1 MΩ, respectively) being in parallel with the load. The error for Case 2 is approximately −90 Ω 15 since $R_{sense}$ is actually 1.1 kΩ. At high frequencies, the error increases for all cases due to gain roll-off in the instrumentation amplifier and voltage buffer as well as the presence of $C_{shunt}$. None of the sources is able to provide good estimates of the load resistance at 1 MHz.

Figure 10B:
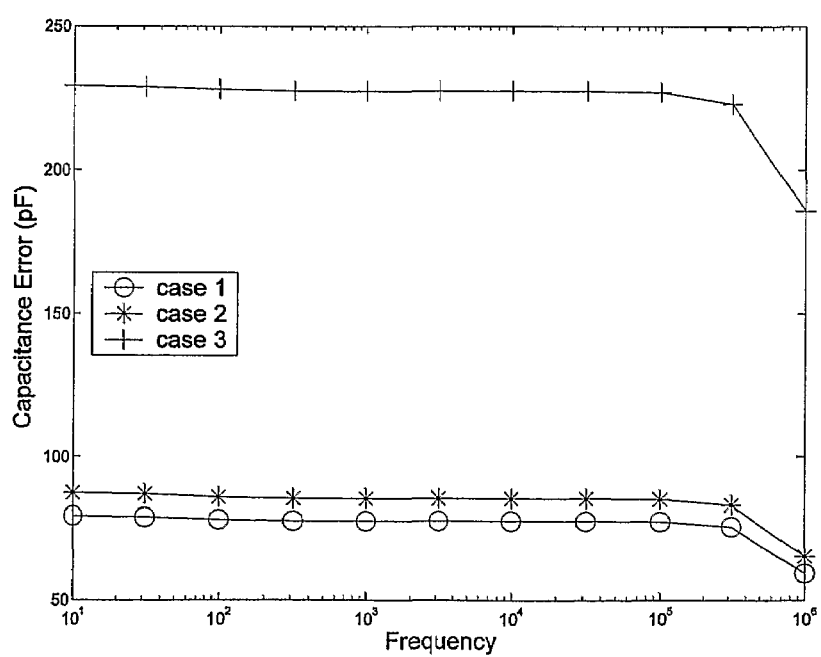
FIG. 10b is a graph showing the error in the estimated load capacitance when three sample voltage sources are operated without calibration according to a simulation.

FIG. 10(b) shows the error in estimated load capacitance. Since the actual load capacitance is zero, the error reflects the actual measured load capacitance. The errors are large and vary with both $R_{sense}$ and $C_{shunt}$. Note that the capacitance that is observed is smaller than $C_{shunt}$ as a result of the limited bandwidth of the instrumentation amplifier and voltage buffer.

Full Calibration: In this simulation, performance with full calibration is also considered, meaning that the calibration circuit itself has been calibrated. Pspice is used to find the complex transimpedance and complex gain of the I-V converter and voltage buffer, respectively, in the calibration circuit. These values were then used to correct the measured values of $I_{cal}$ and $V_{cal}$ to give accurate representations of the voltage and current seen by the calibration circuit.

Figure 11A:
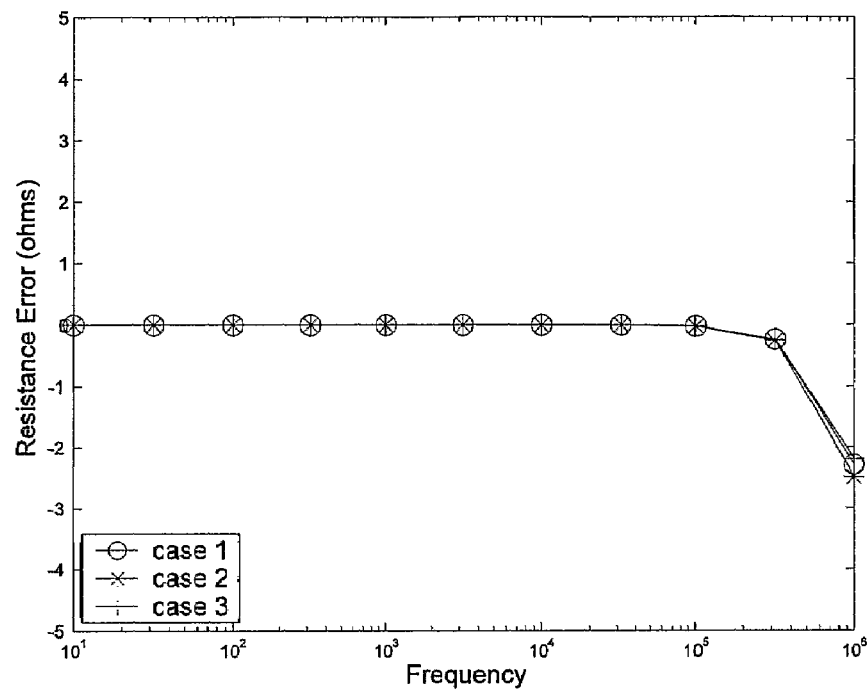
FIG. 11a is a graph showing the error in the estimated load resistance when three sample voltage sources are operated with full calibration according to a simulation.
Figure 11B:
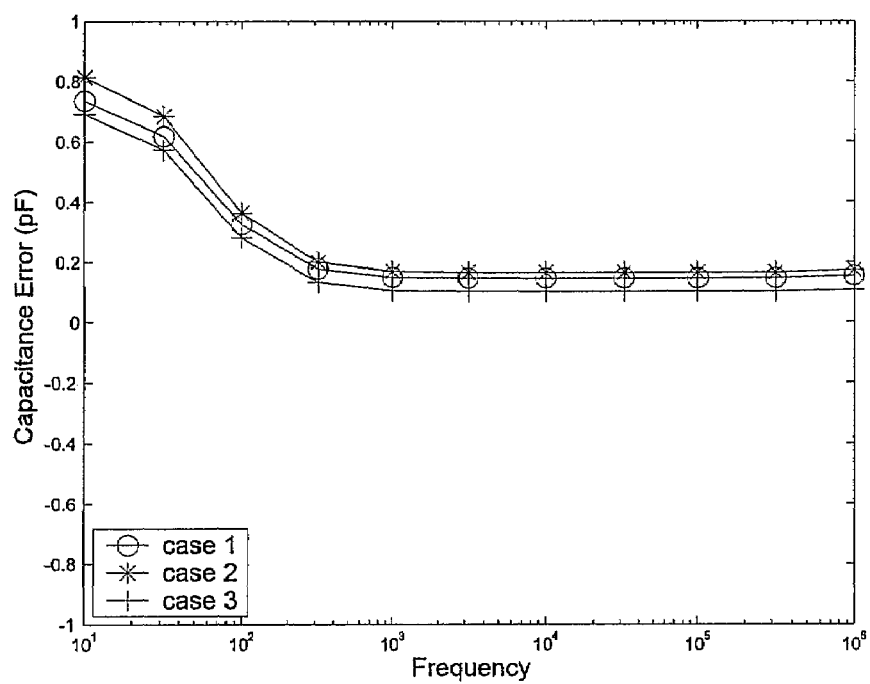
FIG. 11b is a graph showing the error in the estimated load capacitance when three sample voltage sources are operated with full calibration according to a simulation.

FIG. 11 shows the estimated load resistance and capacitance with full calibration. Now, there is only a small error in the estimate of the load resistance at low frequencies (<<0.5 mΩ) and a few ohms of error at high frequencies. It is important to note that the error at high frequencies is nearly the same for all three cases. The errors in the estimate of the load capacitance are generally less than 0.2 pF, though they are somewhat higher at low frequencies.

The performance of the algorithm is limited somewhat by the imperfect virtual ground presented by the I-V converter. The analysis leading to equation 15 takes into account the current through $Z_{shunt}$ that results from having a non-zero voltage across it, it does not account for current that flows through the input and stray capacitance between the input of the I-V converter and ground. Consequently, the I-V converter will provide a low value for the current.

Relative Calibration: In practice, the calibration circuit may not be perfectly calibrated. A feature of the calibration algorithm is that all voltage sources are calibrated using the same calibration circuit, so while errors in calibration circuit calibration will impact the accuracy of the voltage sources, it should not impact their precision. To illustrate this point, the voltage sources were calibrated using a completely uncalibrated calibration circuit. In the calibration algorithm, the I-V converter is assumed to have a frequency independent transresistance of $R_f$ and the voltage buffer is assumed to have a gain of unity.

Figure 12A:
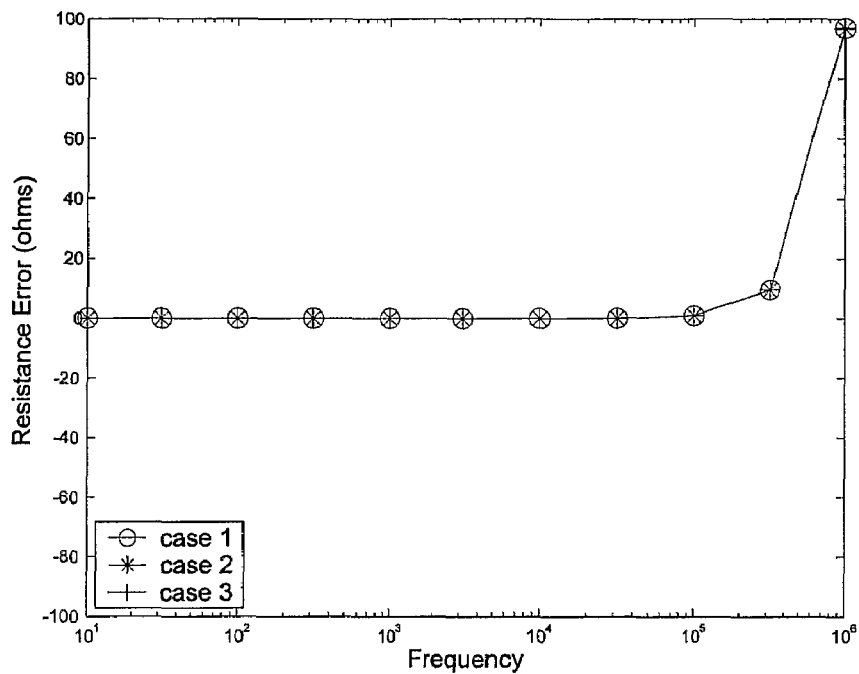
FIG. 12a is a graph showing the error in the estimated load resistance when three sample voltage sources are operated with relative calibration according to a simulation.

FIG. 12 shows the result with an uncalibrated calibration circuit. The absolute error in the estimate of the load resistance is small at low frequencies since $R_f$ actually equals the assumed value of 1 kΩ. At high frequencies the absolute error is much larger due to the uncalibrated frequency response of the calibration circuit. The spread in the error in the estimate of the load resistance, however, is very small at low frequencies (≈0.5 mΩ) and somewhat larger (≈0.5Ω) at high frequencies. The estimate of the load capacitance shows a bias of approximately −50 pF. This bias is due to the fact that the I-V converter uses a 50 pF capacitance in parallel with $R_f=1$ kΩ. Since the I-V converter was not calibrated, the calibration algorithm attributes this RC time constant (with a sign inversion) to the load resistance. Varying the load resistance results in a change in the estimated load capacitance which maintains this same RC time constant. The spread of the estimated capacitance values is less than 0.1 pF across the frequency range shown.

Figure 12B:
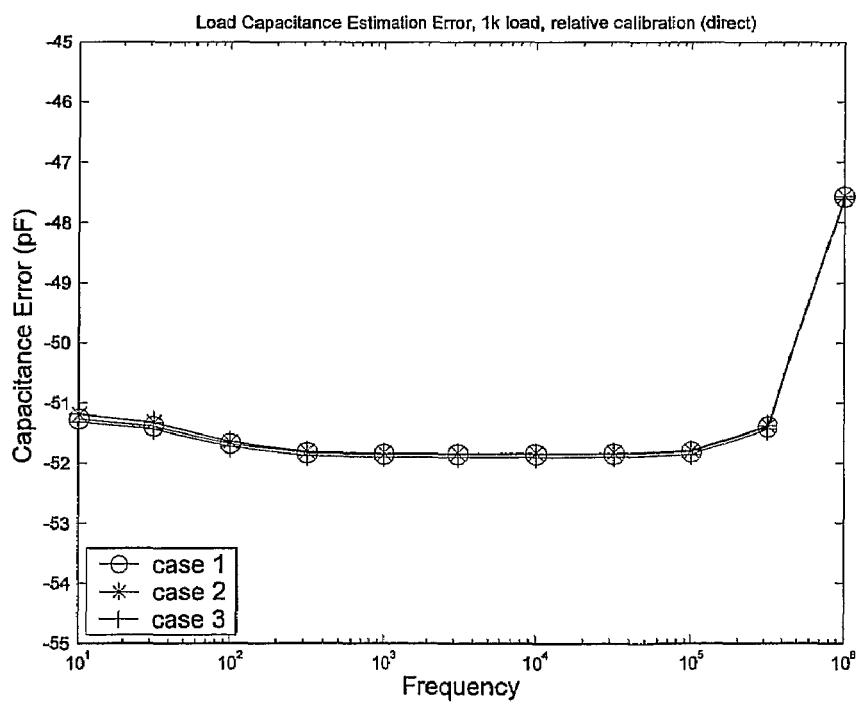
FIG. 12b is a graph showing the error in the estimated load capacitance when three sample voltage sources are operated with relative calibration according to a simulation.

Generally, the calibration circuit would be calibrated, though imperfectly, resulting in smaller errors in accuracy than those observed in FIG. 12. However as FIG. 12(b) shows, even with large errors in accuracy, the relative precision of the voltage sources which are all calibrated using the single calibration circuit remains high.

The results obtained using data from PSpice demonstrate the ability of the calibration system to determine the calibration parameters needed for high-precision voltage source performance. If the calibration circuit is properly calculated, the calibrated voltage sources will also be highly accurate. If the calibration circuit is imperfectly calibrated, the accuracy of the calibrated voltage sources is also imperfect but all sources maintain a high relative precision, since all sources are inaccurate in the same way. In an EIT system, this relative precision of the sources is much more important than the accuracy of the sources. If, for instance, the measured currents at each voltage source are scaled by a single common scaling factor, i.e. the system has high relative precision but does not have high accuracy, the impedance values in the resulting EIT image would also be scaled but the image itself would not be distorted. If, on the other hand, the measured currents at each voltage source are scaled by different scaling factors, representing the case of low accuracy and low relative precision, the image itself would be distorted.

While a specific embodiment of the invention has been shown and described in detail to illustrate the application of the principles of the invention, it will be understood that the invention may be embodied otherwise without departing from such principles.

What is claimed is:

1. An apparatus comprising:
   a plurality of voltage sources for supplying a corresponding plurality of voltages to a corresponding number of other structures;
   voltage source calibration means for calibrating each voltage source; and
   switching means for individually connecting the calibration means to each voltage source in succession during a period when each other structure is in an inactive condition;
   each voltage source including an operational amplifier having an output and a sense resistor connected to the output of the operational amplifier, each voltage source also including a buffer amplifier having an input connected to the sense resistor for outputting a measured voltage, and an instrumentation amplifier having one input connected to the operational amplifier output and another input connected to the sense resistor for outputting a measured current.

2. The apparatus of claim 1, wherein each voltage source has a shunt impedance and includes an ammeter for use in determining an actual current at an output of said voltage source as a function of said shunt impedance.

3. The apparatus of claim 2, wherein each voltage source includes a voltmeter for measuring an actual voltage in said voltage source.

4. The apparatus of claim 1, wherein each voltage source includes a voltmeter for measuring an actual voltage in said voltage source.

5. The apparatus of claim 1, wherein the other structures are a plurality of electrodes that are each adapted to be in contact with a surface of a body to be imaged using electrical impedance imaging, the inactive condition being when the electrodes are not connected to the voltage sources or when the electrodes are out of contact with the body.

6. The apparatus of claim 1, wherein said calibration means comprises a second buffer amplifier and a second operational amplifier, said switching means including a plurality of switches for selectively connecting an output of each voltage source to only one of the second buffer and second operational amplifiers for calibrating respective voltages and currents for each voltage source to compensate for shunt impedance of each voltage source.

7. The apparatus of claim 1, wherein said switching means comprises at least one reed relay in at least one of said calibration means and said voltage sources.

8. A method for calibrating an apparatus having a plurality of voltage sources for supplying a corresponding plurality of voltages to a corresponding number of other structures, and voltage source calibration means for calibrating each voltage source, the method comprising:
   individually connecting the calibration means to each voltage source in succession during a period when each other structure is in an inactive condition for calibrating all of said voltage sources in the same way;
   each voltage source including an operational amplifier having an output and a sense resistor connected to the output of the operational amplifier, each voltage source also including a buffer amplifier having an input connected to the sense resistor for outputting a measured voltage, and an instrumentation amplifier having one input connected to the operational amplifier output and another input connected to the sense resistor for outputting a measured current, the method including determining a gain for the buffer amplifier.

9. A method according to claim 8, wherein the other structures are a plurality of electrodes that are each adapted to be in contact with a surface of a body to be imaged using electrical impedance imaging, the inactive condition being when the electrodes are not connected to the voltage sources or when the electrodes are out of contact with the body.

10. A method according to claim 9, including determining an actual current delivered to the body by the voltage source.

11. A method according to claim 8, including determining a gain for the instrumentation amplifier.

12. A method according to claim 11, including determining a value for the sense resistor.

13. A method according to claim 12, including determining an output shunt impedance for each voltage source.

14. An electrical impedance imaging apparatus comprising:
   a plurality of voltage sources with shunt impedances for supplying a corresponding plurality of voltages to a corresponding number of other structures, each voltage source including an operational amplifier having an output and a sense resistor connected to the output of the operational amplifier, a buffer amplifier having an input connected to the sense resistor for outputting a measured voltage, and an instrumentation amplifier having one input connected to the operational amplifier output and another input connected to the sense resistor for outputting a measured current;
   voltage source calibration means for calibrating each voltage source; and
   switching means for individually connecting the calibration means to each voltage source in succession during a period when each other structure is in an inactive condition.

15. The electrical impedance imaging apparatus of claim 14, wherein said switching means comprises at least one reed relay in at least one of said calibration means and said voltage sources.

16. The electrical impedance imaging apparatus of claim 14, wherein the other structures are a plurality of electrodes that are each adapted to be in contact with a surface of a body to be imaged using electrical impedance imaging, the inactive condition being when the electrodes are not connected to the voltage sources or when the electrodes are out of contact with the body.

17. The electrical impedance imaging apparatus of claim 14, wherein each voltage source has a shunt impedance and includes an ammeter for use in determining an actual current at an output of said voltage source as a function of said shunt impedance.

18. The electrical impedance imaging apparatus of claim 17, wherein each voltage source includes a voltmeter for measuring an actual voltage in said voltage source.

19. The electrical impedance imaging apparatus of claim 14, wherein each voltage source includes a voltmeter for measuring an actual voltage in said voltage source.

20. The electrical impedance imaging apparatus of claim 14, wherein said calibration means comprises a second buffer amplifier and a second operational amplifier, said switching means including a plurality of switches for selectively connecting an output of each voltage source to only one of the second buffer and second operational amplifiers for calibrating respective voltages and currents for each voltage source to compensate for shunt impedance of each voltage source.

\* \* \* \* \*